US006248774B1

(12) United States Patent
Leung (10) Patent No.: US 6,248,774 B1
(45) Date of Patent: Jun. 19, 2001

(54) METHOD FOR TREATING HYPER-EXCITED SENSORY NERVE FUNCTIONS IN HUMANS

(75) Inventor: Edward Leung, Cary, NC (US)

(73) Assignee: King Pharmaceuticals Research & Development, Inc.

( * ) Notice: Subject to any disclaimer, the term of this patent is extended or adjusted under 35 U.S.C. 154(b) by 0 days.

(21) Appl. No.: 09/654,994

(22) Filed: Sep. 5, 2000

(51) Int. Cl.$^7$ .................................................. A61K 31/38
(52) U.S. Cl. .............................................................. 514/443
(58) Field of Search .............................................. 514/443

(56) References Cited

U.S. PATENT DOCUMENTS 5,939,432 * 8/1999 Baraldi ................................. 514/301

* cited by examiner

Primary Examiner—Raymond Henley, III
(74) Attorney, Agent, or Firm—Roberts Abokhair & Mardula, LLC (57) ABSTRACT

A method of and a formulation for treating hyper-excited sensory nerve functions are provided. The method comprises administering to a patient in need of treatment thereof a pharmaceutical composition comprising an effective amount of 2-Amino-4,5,6,7-tetrahydrobenzo[b]thiophen-3-yl)(4-chlorophenyl) methanone or a pharmaceutically acceptable salt thereof. The disorder treated include hyperesthesia, dysesthesia, allodynia, hyperalgesia, tinnitus, ganglionic dysfunction and combinations thereof. The co-administration of adenosine is not needed. The pharmaceutical preparation is suitable for oral administration. The pharmaceutical preparation is useful in the reduction of neuropathic pain in a conscious human. The use of the pharmaceutical preparation does not result in medically adverse cardiovascular symptoms associated with administration of adenosine.

9 Claims, 6 Drawing Sheets

METHOD FOR TREATING HYPER-EXCITED SENSORY NERVE FUNCTIONS IN HUMANS

The present invention relates to normalization of a pathologically hyper-excited sensory nerve function in a conscious human subject. In particular, the invention relates to a treatment method for reducing or eliminating hyper-excited sensory symptoms such as neuropathic pain. Some examples of neuropathic pain are diabetic neuropathy, post-herpetic neuralgia (shingles), trigeminal neuralgia, pain associated with AIDS infection and treatment, whip-lash pain, pain due to cancer treatment, phantom limb pain, traumatic injury, complex regional pain syndrome and pain due to peripheral vascular disease.

The development of hyper-excited sensory nerve function has been described by Sollevi 1997 (1). These symptoms are often manifested as neuropathic pain. Neuropathic pain is a persistent, chronic pain usually described as a burning, shooting or lancinating sensation without an obvious cause. These symptoms are often associated with damage to nerves or nerve fibers. Such pain is associated with the transmission of abnormal pain signals from injured peripheral nerves to neurons in the brain and spinal cord. Briefly, the sensory nervous system projects signals to the central nervous system (CNS), mediating information from the periphery to the brain. These comprise signals from sensors in peripheral tissues and other organs, sensitive for qualities like touch, temperature changes, vibration, painful stimuli, pressure, vision, hearing, smell, taste and balance. This sensory nervous system is an important physiological control in the subject's relation to the environment. The sensory nervous system can be damaged by various types of trauma, such as infections and mechanical lesions including whip-lash injury, diseases such as diabetes and HIV infection, cancer or HIV treatments. This can result in disturbance in the signal transmission into the CNS, leading to reduced perception of sensory signals (hypoestesia) as well as hyper-function (more excited signals in the CNS) due to some largely unknown changes in the nerve transmission process (neuropathic damage). The neuropathic condition with hyper-excitation is described as a "wind-up" phenomenon and often involves several of the above mentioned sensory functions. This may therefore be associated with decreased thresholds for touch and temperature (hyperesthesia), discomfort in the perception for touch and temperature (dysesthesia), discomfort or pain with touch, pressure and/or temperature stimulation (allodynia), and hypersensitivity to pain stimuli (hyperalgesia), balance disturbance, disturbance of auditory type (tinnitus) as well as ganglionic dysfunction. These types of hyper-reactive sensory nerves may develop after various types of trauma, and are called chronic when persistent for more than 3–6 months.

Adenosine, administered intravenously or intrathecally, has been proposed as a treatment for this sensory nerve hyper-reactivity (1, 2, 3). The objective of the treatment is to restore a normal perception of pain, as well as other sensory functions, in patients suffering from pathological hyper-excitation due to nerve damage.

Adenosine is an endogenous nucleoside present in all cell types of the body. It is endogenously formed and released into the extracellular space under physiological and patho-physiological conditions characterized by an increased oxygen demand/supply ratio. This means that the formation of adenosine is accelerated in conditions with increased high energy phosphate degradation. The biological actions of adenosine are mediated through specific adenosine receptors located on the cell surface of various cell types, including nerves (4). The hyper-reactive nerves increase adenosine release due to an increase in metabolic activity.

$A_1$ receptors are widely distributed in most species and mediate diverse biological effects. The following examples are intended to show the diversity of the presence of $A_1$ receptors rather than a comprehensive listing of all such receptors. $A_1$ receptors are particularly ubiquitous within the central nervous system (CNS), with high levels being expressed in the cerebral cortex, hippocampus, cerebellum, thalamus, brain stem, and spinal cord. Immunohistochemical analysis using polyclonal antisera generated against rat and human $A_1$ adenosine receptors has identified different labeling densities of individual cells and their processes in selected regions of the brain. $A_1$ receptor mRNA is widely distributed in peripheral tissues such as the vas deferens, testis, white adipose tissue, stomach, spleen, pituitary, adrenal, heart, aorta, liver, eye, and bladder. Only very low levels of $A_1$ receptors are thought to be present in lung, kidney, and small intestine.

The present invention relates to a class of compounds known as allosteric modulators or allosteric enhancers. At present, allosteric enhancers have only been described for the Al adenosine receptor (5, 6, 7). No allosteric modulators have been proven effective in neuropathic pain models at any concentration. All the currently known enhancers are derivatives of the 2-amino-3-benzoylthiophenes first described by Bruns et al. (5). These benzoylthiophenes are not agonists at the $A_1$ adenosine receptor (5, 6, 8). Structurally, all known agonists for the $A_1$ adenosine receptor are derivatives of adenosine. The presence of an unmodified ribose ring is essential for agonist activity at the $A_1$ adenosine receptor (9). Benzoylthiophenes are not agonists at the $A_1$ adenosine receptor. Importantly, these compounds are antagonists at the $A_1$ adenosine receptor (5, 6, 7, 8). At low concentrations, these benzoylthiophenes enhance the effect of agonists. At higher concentrations, these compounds act as antagonists. Therefore, the concentration range where these compounds can enhance the effects of agonists is limited (8).

Mechanistically, benzoylthiophenes appeared to enhance $A_1$ adenosine receptor function by stabilizing the high affinity state of the receptor-G-protein complex (8, 10). This property is manifested as an increase in high affinity binding in radioligand binding reactions where an agonist radioligand is used to label the $A_1$ adenosine receptor. An enhancer that increases agonist binding can do so by either accelerating the association of agonist and receptor, or by retarding the dissociation of the "receptor-ligand" complex. Kinetic studies have shown the benzoylthiophenes to retard the dissociation of the "receptor-ligand" complex. In contrast, an agonist, or an antagonist will both compete with the radioligand for the binding site and accelerate the dissociation of the "receptor-ligand" complex (8). Since the benzoylthiophenes only selectively retard the dissociation of the "receptor-ligand" complex when an agonist radioligand is used, the benzoylthiophenes must bind to a site different from the agonist recognition site. This putative site is termed the allosteric site, and presumably, compounds that bind to this site and enhance the agonist effect are termed "allosteric enhancers".

Another challenge is that that wide distribution of adenosine receptors offers both opportunities and drawbacks for therapeutic intervention. As an example, A1 adenosine receptors are found in the CNS, in heart and adipose tissue. Thus, agonists are capable of reducing free fatty acid levels in the blood through their interaction with adenosine A1 receptors on fat cells. This is a useful feature in non-insulin dependent diabetes mellitus. However, the concomitant bradycardia and drop in mean arterial pressure due to interference with cardiovascular adenosine receptors are to be considered as serious side effects.

SUMMARY

An object of the present invention is to provide a therapeutically useful enhancer with improved potency as an enhancer, and preferably, without antagonist property. The present invention describes the discovery of a compound that meets these criteria.

The present invention relates to a composition and a method for the treatment of hyper-excited sensory nerve functions, e.g., neuropathia in human subjects. The treatment method comprises oral administration, intravenous administration, or intrathecal administration of an allosteric enhancer at the adenosine $A_1$ receptor. It is demonstrated that 2-Amino-4,5,6,7-tetrahydrobenzo[b]thiophen-3-yl)(4-chlorophenyl)methanone (Compound A) normalized hyper-excited sensory nerve functions in a model of neuropathic pain.

The present invention relates to the discovery of a potent enhancer and a method of ii alleviation or normalization of a pathologically hyper-excited sensory nerve function in a conscious human patient. The method comprises enteral or parenteral administration of an effective amount of Compound A, an $A_1$ allosteric enhancer, to the patient. Another object of the present invention is to provide a composition comprising an adenosine $A_1$ allosteric enhancer for the manufacture of a medicament for alleviation or normalization of a pathologically hyper-excited sensory nerve function in a conscious human subject. The invention further relates to a pharmaceutical preparation for alleviation or normalization of a pathologically hyper-excited sensory nerve function in a conscious human subject, comprising a selected allosteric enhancer for the adenosine receptor in a pharmaceutically acceptable carrier.

Accordingly, the invention provides a method using an allosteric enhancer for the $A_1$ adenosine receptor as a means to reduce or eliminate neuropathic symptoms in human subjects. An allosteric enhancer for the $A_1$ receptor is preferably administered orally in a tablet, capsule, suspension or other suitable oral dose forms. More rapid pharmacologically effect may be elicited by parenteral administration. For parental administration, it may be administered in a central vein or preferably in a peripheral vein, by a bolus injection. If desired, an allosteric enhancer can also be given intrathecally.

When given orally, a dose range of 100 mg to 1000 mg (approximately 1 to 15 mg/kg free base per dose) can be given to a patient. Doses given parentally will be in the range of 0.01 to 1 mg/kg). This treatment can be individually repeated at regular intervals. The invention is a new principle for alleviation of hypersensitivity of the sensory nerve system e.g. such as the perception of touch, temperature, vibration, pain and pressure on the skin.

The invention further applies to alleviation of hyperfunction of other functions, e.g. visual function, auditory function, olfactory function, taste, balance and ganglionic transmission.

DETAILED DISCRIPTION

The present invention involves a method whereby the effects of endogenous adenosine are selectively enhanced at the $A_1$ adenosine receptors. This selective enhancement will be most noticeable in organs or tissues where adenosine release is increased. We have shown that selective enhancement of the $A_1$ adenosine receptor leads to the restoration of normal sensitivity in a model of neuropathic pain. The mechanism of action for intravenous adenosine is known. Several reports are available explaining the mechanism of how adenosine works. Adenosine has been reported to cause pain (algogenic and hyperalgesic effects) as well as to alleviate pain (antinociceptive or analgesic effects). The mechanisms that are responsible for these opposite effects have been described in Purinergic Approaches in Experimental Therapeutics, edited by Kenneth A. Jacobson and Michael F. Jarvis, Chapter 25 entitled Purines and Nociception, by Jana Sawynok, Wiley-Liss, Inc. 1997. reviewed (14). Briefly, activation of adenosine A2 receptors in sensory nerve fibers leads to a potentiation of the nociceptive signal in several rodent pain models. This is due to a direct activation of the sensory nerve terminals as well as the release of endogenous mediators of pain such as histamine, 5-HT, substance P and other cytokines. In these animal models, adenosine and adenosine A1 agonists alleviate pain by a central mechanism. Specifically, the analgesic effect of adenosine involves the A1 adenosine receptors in the dorsal horn of the spinal cord. This region is where the sensory nerve fibers enter the spinal cord. The pain signals are processed in this area and then transmitted to the brain where the nociceptive signals are interpreted as pain. It is hypothesized that adenosine A1 receptors suppress the nociceptive signal at the afferent nerve terminals, interneurons and the projection neurons in the dorsal spinal cord. In addition to the spinal mechanism of analgesia, administration of adenosine or A1 agonists directly into the brain also produces analgesia. Therefore, supraspinal mechansims may also contribute to the analgesia produced by adenosine and an allosteric enhancer. The new treatment, in accordance with one embodiment of the present invention, using the $A_1$ allosteric enhancer allows an oral medication that can be given daily. Additionally, the present invention is applicable to other pharmaceutical methods for the delivery of the compound to a target area including topical applications.

One major side effect of adenosine for neuropathic pain is in the delivery. Present pharmaceutical applications of adenosine do not include oral administration and are limited to being administered by IV injection or intrathecal injection. The advantage of the present invention is that the composition (including T62) is delivered as an IV injection, intrathecal injection or by oral administration. Further, adenosine can only be delivered within a limited dose range by IV injection. For example, reference number 2 explained that at dose-rate above 70 microgram per kilogram per minute (μg/kg/min.), symptoms similar to angina pain are experienced. The lowest documented dose for efficacy for adenosine is 35 μg/kg/min. As can be seen, the therapeutic window of adenosine given intravenously only appears to have a two fold window for efficacy. Adenosine cannot be given as a bolus injection to reduce pain. Bolus adenosine has the potential to cause heart block, which is not a desired outcome. Therefore, the reduced side effect of the present invention when compared to adenosine, include the following: a greater window of therapeutic doses without causing angina pain, avoid the need for intravenous injection, and a patient is able to administer the drug through oral doses. Additionally, topical applications are allowed based on the effectiveness of T62 as a modulator and not as an antagonist over a broader dosage range. This is particularly true since T62 is effective as a modulator over the higher doses and does not behave as an antagonist at those doses. Topical application include using a formulation including T62 for wound healing.

Even though there are many potential therapeutic benefits for an allosteric enhancer over an agonist for the $A_1$ adenosine receptor (10), the most potent enhancer generally known is still PD 81,723 (5, 8) first described in 1990. One explanation for the lack of progress in this field is that the enhancing action of the benzoylthiophenes is difficult to quantify. In addition, the effect of enhancers appears to be dependant on the type of test performed. In the demonstration of the applicability of the present invention, we demonstrated the following:

1. Binding studies in test tubes are not predictive of functional enhancement in cells or isolated tissues.

2. Functional studies conducted in whole cells revealed that the A1 allosteric modulator of the present invention is a potent enhancer.

3. The $A_1$ allosteric modulator or enhancer or the present invention alleviates neuropathic pain in a dose dependant, time dependant manner in a rodent model of neuropathic pain.

4. The $A_1$ allosteric enhancer of the present invention is also active when given via the intrathecal route and intraperitoneal route.

5. The $A_1$ allosteric enhancer of the present invention is effective over a wider dosage range, particularly at higher concentrations, to allow application in oral or topical pharmaceutical compositions.

In the work of Bruns et al. (5, 8), enhancement at the $A_1$ adenosine receptor was determined by the following methods: (a) radioligand binding at the $A_1$ receptor in rat forebrain membranes; and (b) cyclic AMP accumulation in FRTL-5 thyroid cells of the rat. Van der Klein et al. (6) also employed binding at the rat $A_1$ receptor as the method for detecting enhancement for a series of benzoylthiophenes. In both studies, 2-Amino-4,5,6,7-tetrahydrobenzo[b]thiophen-3-yl)(4-chlorophenyl)methanone (Compound A) was described (compound 30 in (5) and compound 12N in (6)) as an enhancer with $ED_{50}$ values of 15.3 and 6.8 micromolar, respectively. In both studies, compound A was reported to be an antagonist with affinity values in the 2 to 10 micromolar range. Based on these results, one skilled in the art is led to the conclusion that compound A is not a potent enhancer.

From the known literature, Compound A is also not a useful lead because of the small separation between enhancer effects and antagonism at the $A_1$ receptor. Indeed, the best compound that has come out of these investigations is PD 81,723 (5, 6, 8, 10).

There is evidence in the literature that binding studies are not internally consistent and they also do not necessarily predict functional enhancement in vitro. For example, PD 78,416 retards the dissociation of [$^3$H]CHA binding in rat brain (8). However, enhancement of [$^3$H]CHA binding was not observed in rat brain in competition studies. In functional studies conducted in the isolated guinea pig left atrium and isolated ileum, PD 78,416 enhanced the effect of the agonist $N^6$-cyclopentyladenosine (CPA) in the left atrium. However, the same compound failed to enhance the effect of CPA in the isolated ileum (11). Taken together, these data point to the difficulties in predicting functional enhancement at the $A_1$ adenosine receptor.

We used the cloned human $A_1$ adenosine receptor as a tool for assaying functional enhancement produced by benzoylthiophenes (12). By this method, we have identified that compound A is a potent enhancer at the cloned human A1 adenosine receptor. Importantly, this compound does not antagonize the A1 receptor even at a 10 micromolar concentration.

The following experiments show the effect of compound A on cyclic AMP production in CHO cells expressing the $A_1$ adenosine receptor. Chinese hamster ovary cells expressing human recombinant $A_1$ adenosine receptors (CHO: hu A1 cells) at a density of approximately 8000 fmol/mg protein were prepared as previously described (12) and aliquots of these cells at low passage numbers were frozen and stored in liquid nitrogen. Cells were removed from liquid nitrogen storage when needed, and grown in Ham's F-12 culture medium with 10% fetal bovine serum and 0.5 mg/ml of antibiotic G-418. Aliquots of cells were placed into 12-well cultured plates with culture medium, serum, and antibiotic for 48-72 hours, by which time the cells had grown to a confluent monolayer. To begin an experiment, growth medium was removed from the culture plates and cells were washed once with Hanks' buffered saline solution. The wash solution was then removed and replaced with fresh Hanks' solution containing forskolin (1 μM), rolipram (20 μM), CPA (0.05 or 1 nM), adenosine deaminase (2 U/mL), and the allosteric enhancer to be tested. After 6 min of incubation at 36° C. in the presence of drugs, the incubation solution was removed and hydrochloric (final concentration, 50 mM) was added to terminate drug action. The content of cAMP in acidified extracts of cells was determined by radioimmunoassay as previously described (12). The compounds listed in reference 7 (U.S. Pat. No. 5,939,432) relating to allosteric enhancers, were tested using this method. None of these agents showed the high potency and the benefits seen with T62, the compound of the present invention.

Figure 1:
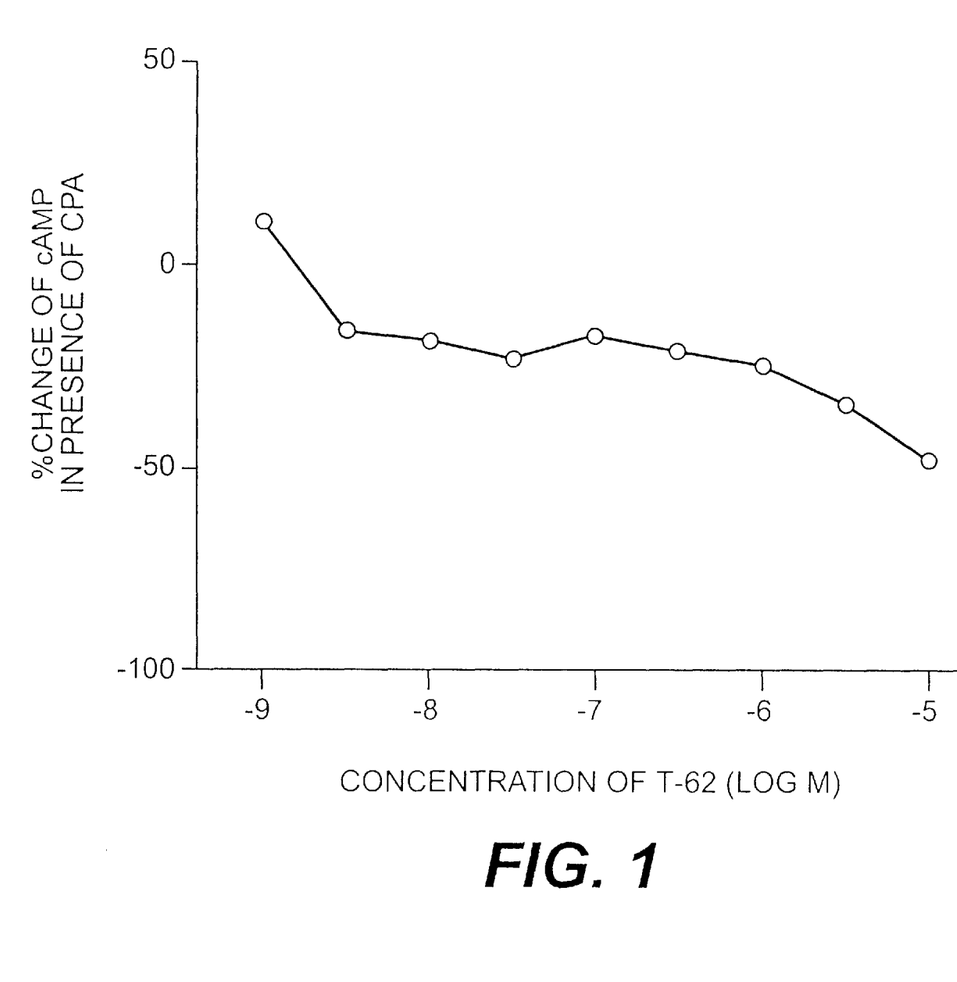
FIG. 1 is a graphic representation showing the percentage change of cAMP (adenosine 3',5'-cyclic monophosphate) in presence of CPA ($N^6$-cyclopentyladenosine) in relation to T62 concentration in accordance with one embodiment of the present invention.

Because the magnitude of the effects of allosteric enhancers on cells changed with time and batch of cells, the actions of each test compound to enhance the effect of CPA (and thus reduce cAMP content of CHO cells) were normalized to the response of cells to 10 μM PD 81,723. FIG. 1 shows enhancement of the CPA induced inhibition of cyclic AMP production by compound A. Enhancement by compound A began at 10 nM. There was no antagonism of this effect even at 10 μM of compound A. This study shows compound A to be a more potent enhancer than PD 81,723. Also, because compound A does not antagonize the $A_1$ adenosine receptor in vitro, it has a better therapeutic potential compared to PD 81,723 and other enhancers that have been reported (5, 6, 7).

The effects of the compound of the present invention on a rodent model of neuropathic pain were demonstrated as discusses below. Following Animal Care and Use Committee approval, mechanical hypersensitivity was generated in male Sprague-Dawley rats as described in the following paper. (Kim, S. H. and Chung, J. M., An experimental model for peripheral neuropathy produced by segmental spinal nerve ligation in the rat, Pain, 50 (1992) 355–363. Briefly, under general anesthesia with inhalational halothane, the left L5 and L6 spinal nerves were identified through a small laminotomy and tightly ligated. Approximately one week later, an intrathecal catheter was placed under general anesthesia by insertion under direct vision of a polyethylene catheter through a small slit in the dura at the cisterna magnum and advanced 8.5 cm such that the catheter tip resided in the lower lumbar intrathecal space. Animals were studied approximately one week later.

Ligation of the lumbar spinal nerves results in a primarily unilateral increase in the sensitivity to light touch on the operated side. Sensitivity was assessed via application of calibrated von Frey filaments. The withdrawal threshold was determined using an up down method as described in Chaplan, S. R., Bach, F. W., Pogrel, J. W., Chung, J. M., and Yaksh, T. L., Quantitative assessment of tactile allodynia in the rat paw, J. Neurosci. Methods, 53 (1994) 55–63. In general, withdrawal threshold is 35 g or greater in animals prior to surgery, which is markedly reduced to <4 g within one week of spinal nerve ligation, and this hypersensitivity is stable for several weeks thereafter. Von Frey filaments are scientific apparatus designed to apply a predetermined pressure to a surface. These filaments are flexible bristles with a flat tip. The applied pressure is determined by the diameter of the filament. In these studies, the animals are placed on top of a wired cage. The goal of these studies is to determine the pressure at which the animal perceives the pressure applied as painful and lifts its foot. The scientist determines the discomfort pressure threshold by pressing the tip of von Frey filaments, one filament at a time, to the bottom of the foot through the wired cage floor. When a slight pressure is applied to the underside of the foot, the animal feels the sensation but it will not lift its foot because this sensation is not painful, or uncomfortable. In a normal animal, the threshold for discomfort is approximately 35 g pressure. In an animal whose foot is rendered more sensitive to pressure, the withdrawal threshold is less than 4 g. That is, a pressure that is not perceived as pain in the unaltered, control foot will be perceived as a painful stimulus in the surgically altered foot. This increase in the pain response is described as hypersensitivity. Considerable research has utilized this model, which mimics several factors present in patients with chronic, neuropathic pain, including reduced sensitivity to opioids but response to alpha2-adrenergic agonists and atypical analgesics including gabapentin.

Adenosine is being continually released in the spinal cord in this model, as evidenced by reduction in hypersensitivity after intrathecal injection of inhibitors of adenosine reuptake or metabolism. We tested the adenosine receptor modulator, compound A, to determine if it would have activity in this model and would potentiate the effects of intrathecal adenosine itself.

Mechanical withdrawal threshold was determined before and at intervals after intrathecal injection of compound A, 1–5 μg. Larger doses resulted in obvious motor blockade. In the study, the investigator was blinded to the dose administered. Compound A was dissolved in cyclodextrin, which had no effect on withdrawal threshold when administered alone. In separate experiments, animals received intrathecal adenosine, 5–30 μg, and the effect of adenosine was compared to that of compound A.

Animals were randomized to receive a single intrathecal injection of the allosteric adenosine receptor modulator of the present invention (referred to as compound A or T62), in doses of 1, 3, or 5 μg. For comparison purposes, adenosine itself was administered in doses of 5, 10, or 30 μg. Doses of T62 and adenosine were determined in pilot experiments to encompass the therapeutically effective range. Animals received 6 injections, each separated by a minimum of 4 days to prevent development of tolerance. The withdrawal threshold to mechanical stimulation with von Frey filaments was determined before and at intervals of 3 hours following intrathecal injection, then again at 20 hours following injection. A dose response was determined using the time of peak effect (2 hr for each compound) and the ED50 determined by linear regression.

In order to determine the type of interaction between intrathecal adenosine and T62, an isobolographic approach was used. In this design, adenosine and T62 were combined in the ratio of their ED50s and this combination administered in different doses in a constant ratio (adenosine:T62 of 7:1.8 μg, 14:3.5 μg, or 24:6 μg). The ED50 for the mixture (total of each component combined) was determined by linear regression, an isobologram constructed, and the observed ED50 was compared to the theoretical ED50 by a t-test as previously described in Tallarida, R. J., Statistical analysis of drug combinations for synergism, Pain, 49 (1992) 93–97. In order to determine the site of action of T62, two experiments were performed. First, the effect of intraperitoneal injection of T62, 15 mg/kg, was tested, and was noted to be effective to reduce hypersensitivity. The effect of systemic T62 was then tested following intrathecal injection of the $A_1$ receptor preferring antagonist, 8-cyclopentyl-1,3-dipropylxanthine (DPCPX), 9 μg. This dose has been previously demonstrated to block the effect of adenosine to reduce hypersensitivity in rats following spinal nerve ligation. See Gomes, J. A., Li, X. H., Pan, H. L., and Eisenach, J. C., Intrathecal adenosine interacts with a spinal noradrenergic system to produce antinociception in nerve-injured rats, Anesthesiology, 91 (1999) 1072–1079.

Adenosine $A_1$ agonists produce behavioral sedation and motor blockade when administered in high doses as described in Sosnowski, M., Stevens, C. W., and Yaksh, T. L., Assessment of the role of $A_1/A_2$ adenosine receptors mediating the purine antinociception, motor and autonomic function in the rat spinal cord, J. Pharmacol. Exp. Ther., 250 (1989) 915–922. To screen for these effects, animals receiving drug treatment were observed for changes in normal exploratory behavior when placed on an open surface and were observed for signs of abnormal ambulation.

Drugs employed were adenosine (Adenocard, Fujisawa, Deerfield, Ill.), DPCPX (RBI, Natick, Mass.) and T62 (Medco Research, Inc, Cary, N.C.). T62 was dissolved in 45% 2-hydroxypropyl-ω-cyclodextrin (RBI, Natick, Mass.). Drugs were administered intrathecal in a 5 μl volume followed by 10 μl of saline to flush the catheter.

Data are presented as median ±25th and 75th percentile (for raw withdrawal thresholds) or by mean ±SE. Linear regression was used to calculate the ED50 for each drug alone and for the fixed ratio combination. The ED50 was determined for each animal, rather than a probit analysis of the entire data set. The effect of each agent alone and the combination on withdrawal threshold over time was tested by Kruskal-Wallis analysis. P<0.05 was considered significant.

Figure 2:
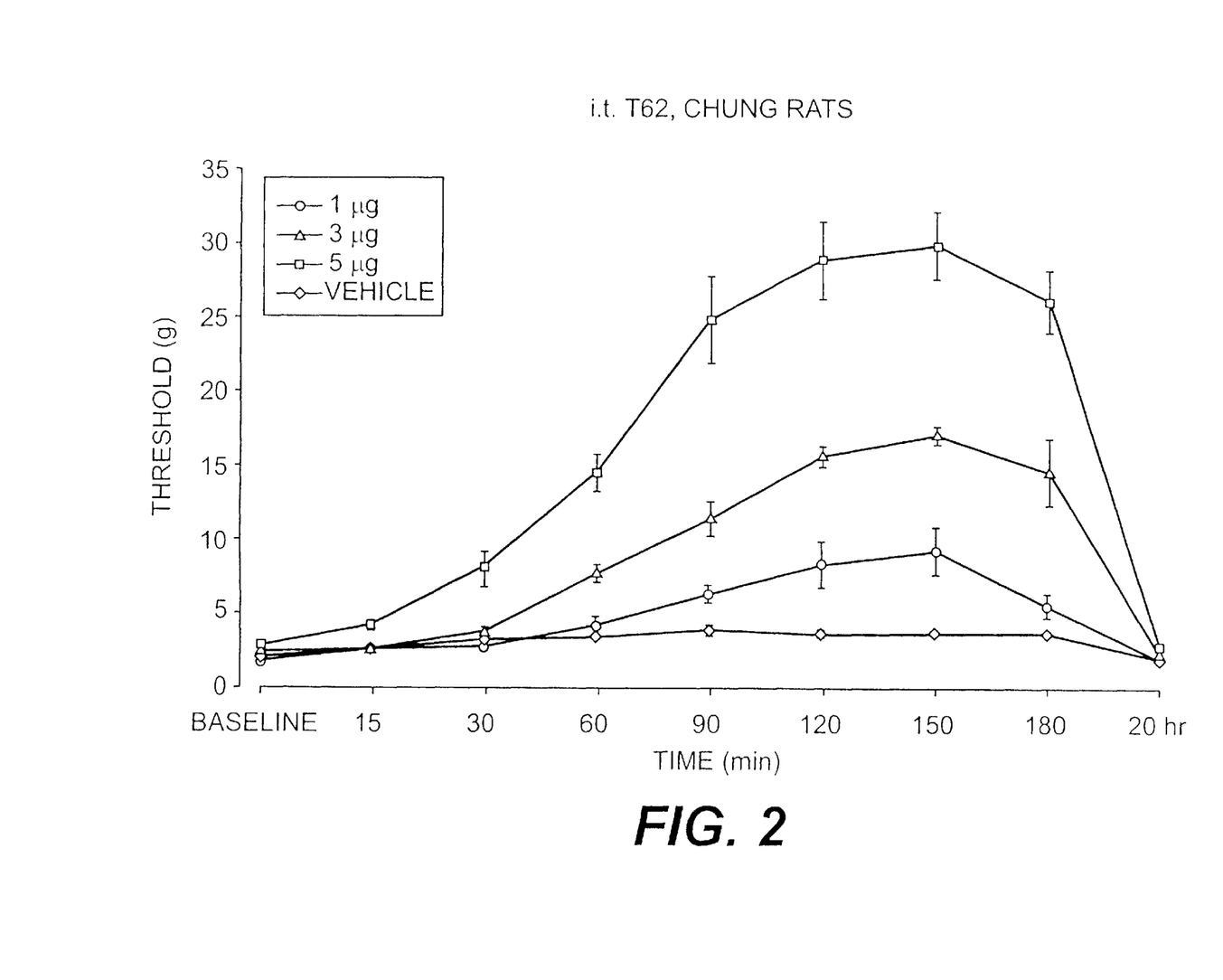
FIG. 2 is a graph showing pain threshold values versus time and T62 concentration in accordance with an embodiment of the present invention.
Figure 3:
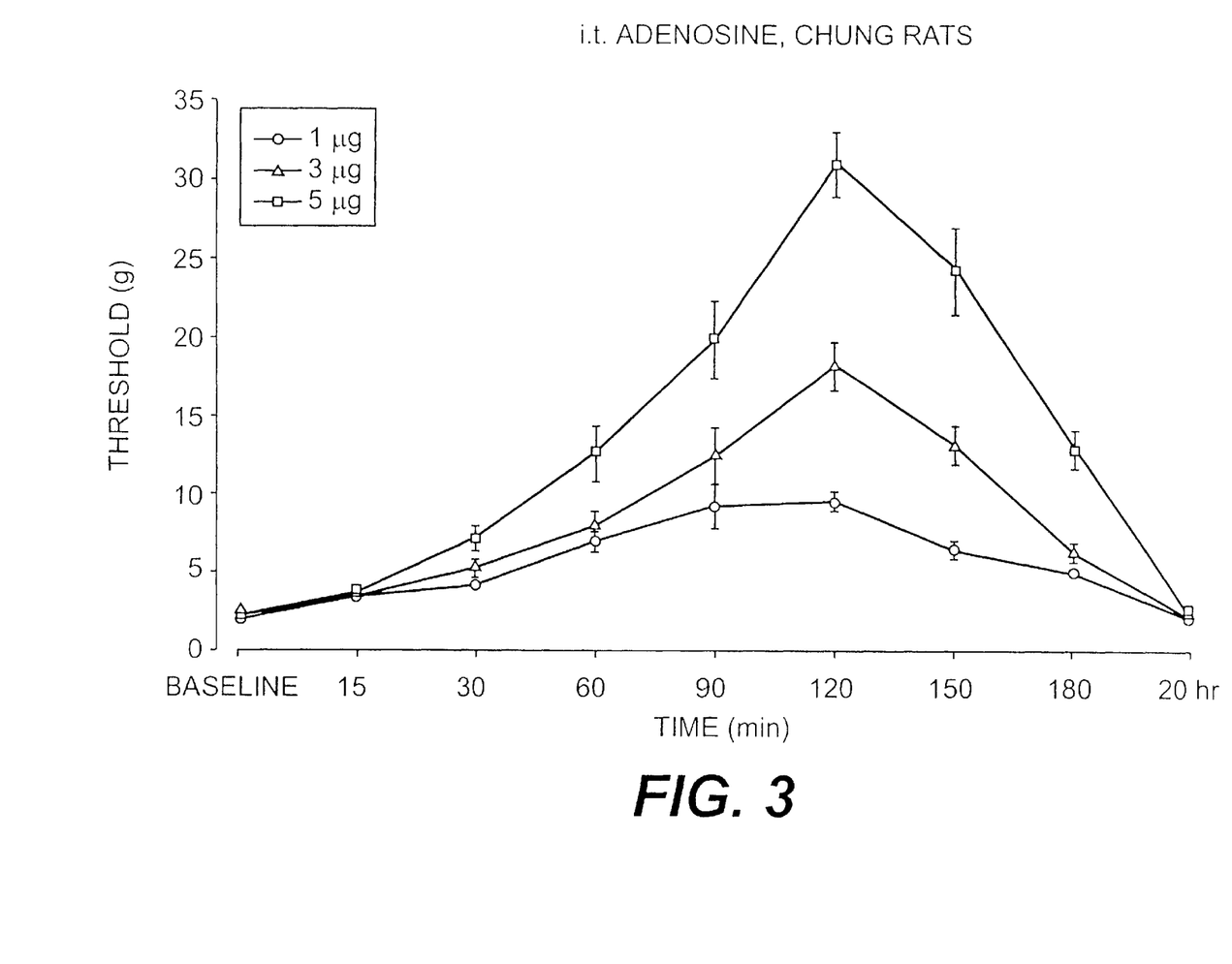
FIG. 3 is a graph illustrating pain threshold variations versus time and adenosine concentrations.
Figure 4:
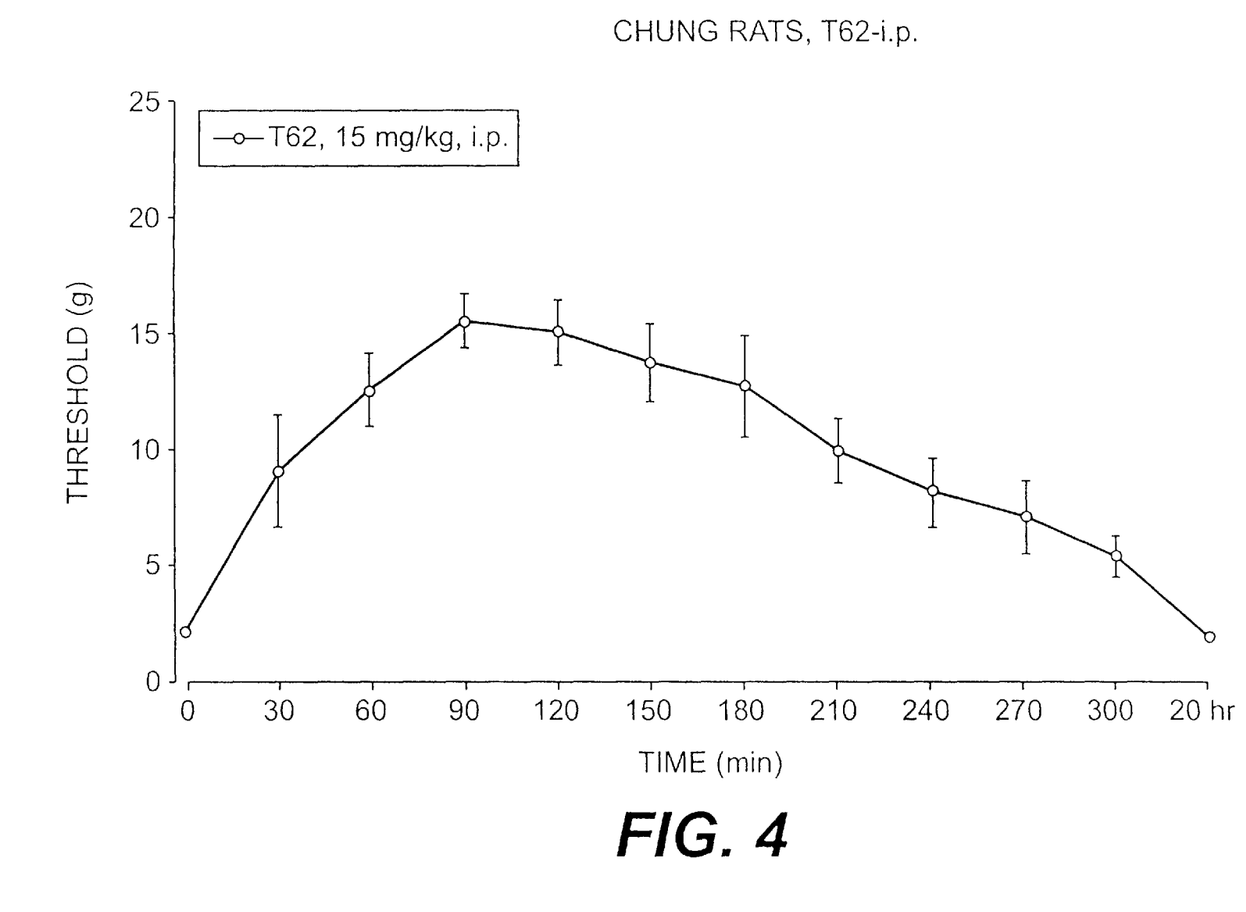
FIG. 4 is a graph illustration of pain threshold values versus time for T62 in accordance with an embodiment of the present invention.
Figure 5:
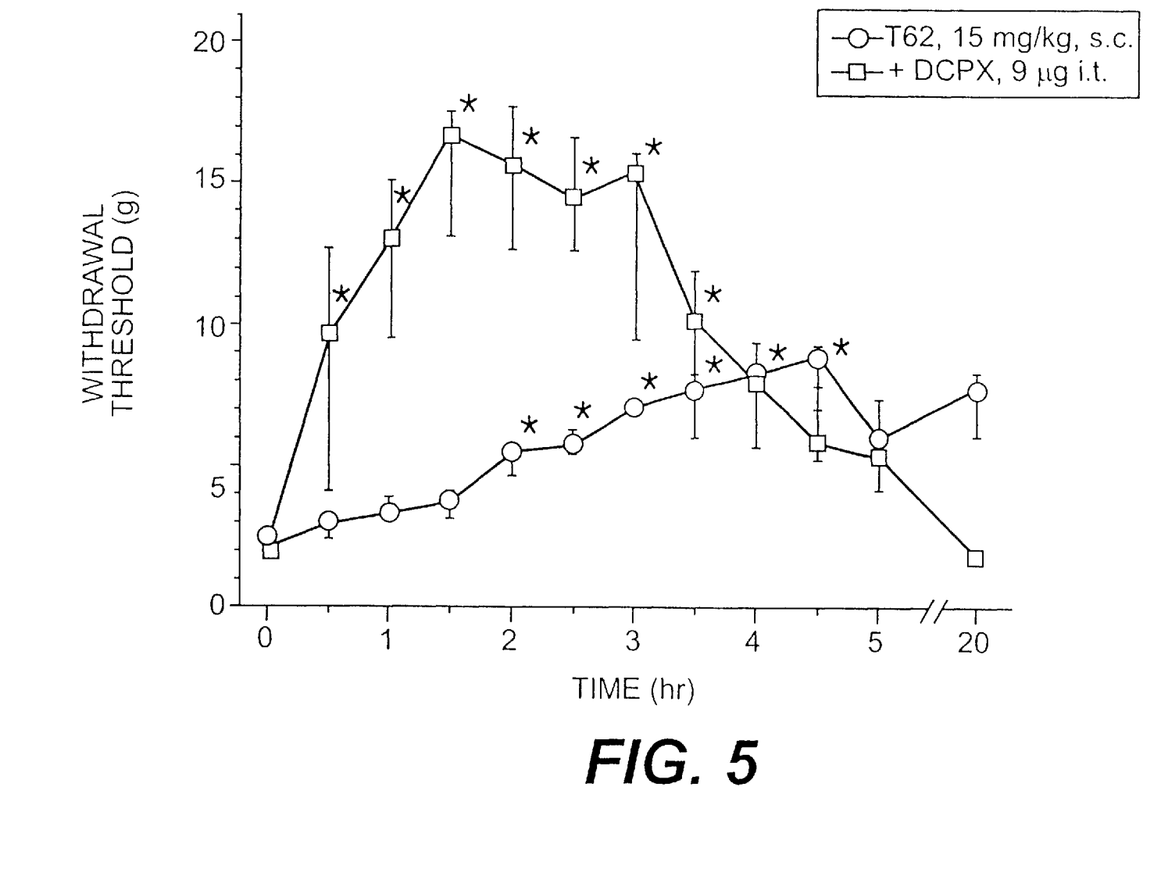
FIG. 5 is a graphical illustration of pain threshold values versus time for T62 in accordance with an embodiment of the present invention.
Figure 6:
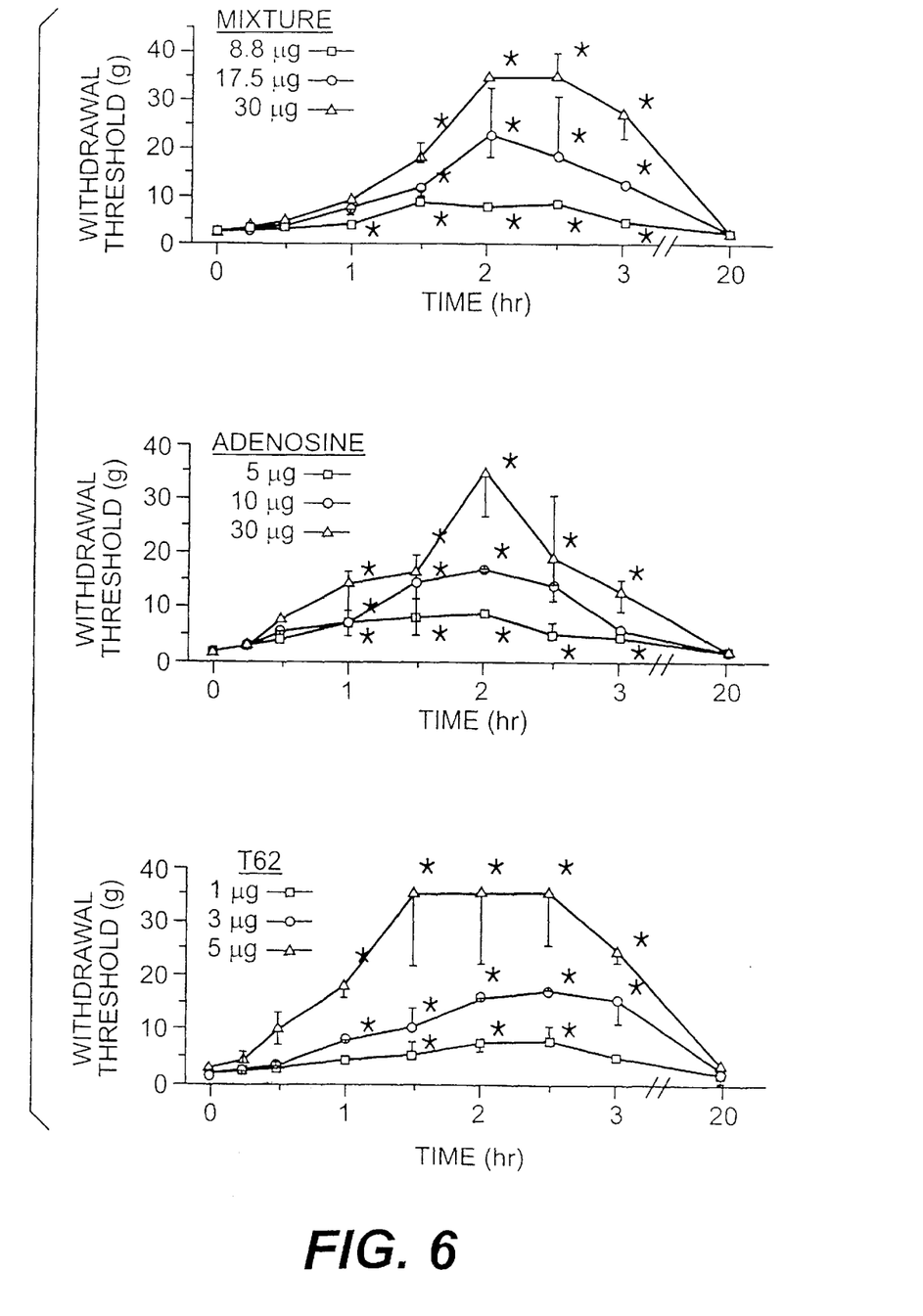
FIG. 6 includes several graphs showing the pain withdrawal threshold values for T62, adenosine, and mixtures thereof versus time illustrating various embodiments of the present invention.

Results are summarized in FIGS. 2, 3, 4, which depict raw data of withdrawal threshold over time as median ±25$^{th}$ and 75$^{th}$ percentiles. FIG. 2 shows intrathecal injection of compound A produced dose- and time-dependent increases in withdrawal threshold, returning sensitivity to normal at the 5 μg. The effect of compound A lasted over 4 hours. FIG. 3 shows a similar experiment where intrathecal adenosine produced a dose-and time-dependent increase in withdrawal threshold, returning sensitivity to normal at the 30 μg dose. FIG. 4 shows the effect of compound A following intraperitoneal injection (IP) at a dose of 15 mg/kg. The effect of compound A following IP injections lasted at least 4 hours. Since compound A (T62) is active after IP injection, an oral formulation containing a dose range around 15 mg/kg is useful in man for treating hyper-excited nerve activities, including neuropathic pain. In addition, the effect of compound A following intraperitoneal injection is blocked by intrathecal administration of the A1 receptor antagonist DPCPX (5 μg). These results confirmed that compound A is producing its effect via actions at the $A_1$ adenosine receptor in the spinal cord. The "star" points in the figures indicate that the values are significantly different from control values. That is to say that the response is considered analgesic.

While the present invention includes the co-administration of adenosine with T62, this co-administration is not essential. It is preferred to administer T62 alone for economic and drug interaction reasons. Adenosine is released from the hyperexcited nerves. The formulation of the present invention (T62) enhances the effect of endogenous adenosine released from the hyperexcited nerves. Because adenosine is not released everywhere all at once, that is why this treatment method provides site specific, event-specific beneficial effects. For example, for the patients suffering from neuropathic pain, the enhancer amplifies the analgesic effect of endogenous adenosine and produces pain relief. This patient will not suffer symptoms of a heart attack because the release of adenosine is not being stimulated in the heart. Topical applications of the present invention also allow the localized usage of the $A_1$ allosteric modulator.

One advantage of the present invention is the ability to use the compound over a wide dosage range with various modes of administration, including oral administration. One of the options includes the administration of T62 as an intravenous bolus injection. For the bolus administration, the preferred dose range is from about 0.1 milligrams (mg) to about 15 mg per kg. The most preferred dose range is from about 1 to about 5 mg per kilogram.

For administration in the form of an oral dose, the preferred range is from I mg to 1000 mg. The most preferred range is from 10 to 500 mg range.

In one embodiment of the present invention, a formulation comprising T62 is administered as a tablet, capsule, caplet, coated tablet, capsule containing various smaller sizes coated particles, and the like. The pill is given as an oral medication once or twice daily for treating symptoms of neuropathic pain. Two per day are an option, one for daytime use and one for nighttime use. Since there is the potential of an enhancer to cause sedation at a high dose, the higher doses are recommended for night use. For example, a dose of from 100 to 500 mg dose of T62 in tablet form is recommended for daytime use while a dose from 600 to 1000 mg is recommended as a nighttime dose.

The following references are indicative of the level of skill in the art and provide background for the present invention. The disclosures of all these references are hereby incorporated by reference in their entirety.

1. Sollevi, A. Method of treating hyperexcited sensory nerve function. U.S. Pat. No. 5,691,318, 1997.

2. Sollevi, A. Adenosine for pain control. Acta Anaesthesiol. Scand. Suppl. 110: 135–136, 1997.

3. Belfrage M, Segerdahl M, Arner S, Sollevi A. The safety and efficacy of intrathecal adenosine in patients with chronic neuropathic pain. Anesth. Analg. 89: 136–142, 1999.

4. Ralevic V. and Bumstock, G. Receptors for Purines and Pyrimidines. Pharmacol. Rev. 50: 413–492, 1998.

5. Bruns, R. F., Fergus, J. H., Coughenour, L. L., Courtland, G. G., Pugsley, T. A., Dodd, J. H., Tinney, F. J. Structure-activity relationships for enhancement of adenosine A1 receptor binding by 2-amino-3-benzoylthiophenes. Mol. Pharm. 38: 950–958, 1990.

6. van der Klein, P. A., Kourounakis, A. P. and Ijzerman, A. P. Allosteric modulation of the adenosine A(1) receptor. Synthesis and biological evaluation of novel 2-amino-3-benzoylthiophenes as allosteric enhancers of agonist binding. J Med Chem 42: 3629–3635, 1999.

7. Baraldi, P. G. Thiophenes useful for modulating the adenosine receptor. U.S. Pat. No. 5,939,432, 1999.

8. Bruns,R. F. and Fergus, J. H. Allosteric enhancement of adenosine A1 receptor binding and function by 2-amino-3-benzoylthiophenes. Mol. Pharmacol. 38: 939–949, 1990.

9. Poulsen, S. A. and Quinn, R. J. Adenosine receptors: new opportunities for future drugs. Bioorg. Med. Chem. 6:619–641, 1998.

10. Linden, J. Allosteric enhancement of adenosine receptors. In Purinergic Approaches in Experimental Therapeutics, Edited by K. A. Jacobson and M. F. Jarvis, 1997 Wiley-Liss, pp8514 97.

11. Leung, E. Walsh, L. K. M., Flippin, L. A., Kim, E. J., Lazar, D. A., Seran, C. S., Wong, E. H. F. and Eglen, R. M. Enhancement of adenosine A1 receptor functions by benzyoylthiophens in guinea pig tissues in vitro. Naunyn-Schmiedeberg's Arch. Pharmacol. 352: 206–212, 1995.

12. Shryock, J. C., Ozeck, M. J. and Belardinelli, L. Inverse agonists and neutral antagonists of recombinant human A1 adenosine receptors stably expressed in chinese hamster ovary cells. Mol. Pharmacol. 53: 886–893, 1998.

13. Kim, S. H. and Chung, J. M. An experimental model for periphereal neuropathy produced by segmental spinal nerve ligation in the rat. Pain, 50: 355–363, 1992.

14. Sawynok J. Purines and Nociception. In Purinergic Approaches in Experimental Therapeutics, Edited by K. A. Jacobson and M. F. Jarvis. 1997 Wiley-Liss, pp495–513.

The present invention comprises the compound described above as T62 or Compound A. Suitable components for the present invention are represented by the following formula and pharmaceutically acceptable salts thereof.

"Pharmaceutically acceptable salts" refers to pharmaceutically acceptable salts of a compound A, which salts are derived from a variety of organic and inorganic counter ions well known in the art and include, by way of example only, sodium, potassium, calcium, magnesium, ammonium, tetraalkylammonium, and the like; and salts of organic or inorganic acids, such as hydrochloride, hydrobromide, tartrate, mesylate, acetate, maleate, oxalate and the like can be used as the pharmaceutically acceptable salt. Pharmaceutically acceptable salts of compound A are within the scope of the present invention. As will be understood by those skilled in the art, pharmaceutically acceptable salts include, but are not limited to, salts with inorganic acids such as hydrochloride, sulfate, phosphate, hydrobromide, and nitrate or salts with an organic acid such as malate, maleate, fumarate, tartrate, succinate, citrate, acetate, lactate, methanesulfonate, p-toluenesulfonate, palmoate, salicylate, and stearate. Other acids such as oxalic, while not in themselves pharmaceutically acceptable, may be useful as intermediates in obtaining the compounds of the invention and their pharmaceutical salts.

What is claimed:

1. A method of treating hyper-excited sensory nerve functions, comprising administering to a patient in need of treatment thereof a pharmaceutical composition comprising an effective amount of 2-Amino-4,5,6,7-tetrahydrobenzo[b]thiophen-3-yl)(4-chlorophenyl) methanone or a pharmaceutically acceptable salt thereof.

2. The method of claim 1 the pharmaceutical composition is administered to a conscious human patient in a dose of greater than 5 $\mu$/kg/min.

3. The method of claim 1 the pharmaceutical composition is administered to a conscious human patient in a dose of greater than 10 $\mu$g/kg/min.

4. The method of claim 1 wherein the disorder to be treated is selected from the group consisting of hyperesthesia, dysesthesia, allodynia, hyperalgesia, tinnitus, ganglionic dysfunction and combinations thereof.

5. A method of treating hyper-excited sensory nerve functions, comprising administering to a patient in need of treatment thereof an effective amount of a pharmaceutical composition comprising the compound 2-Amino-4,5,6,7-tetrahydrobenzo[b]thiophen-3-yl)(4-chlorophenyl) methanone or a pharmaceutically acceptable salt thereof and adenosine.

6. The method of claim 1 wherein the administering to the patient includes administration via topical, oral, intrathecal, and intravenous applications.

7. A method of treating hyper-excited sensory nerve functions, comprising administering to a patient in need of treatment thereof an oral pharmaceutical composition comprising an effective amount of 2-Amino- 4,5,6,7-tetrahydrobenzo[b]thiophen-3-yl)(4-chlorophenyl) methanone or a pharmaceutically acceptable salt thereof.

8. The method of claim 7 wherein the administering to the patient of the oral pharmaceutical composition comprises giving the patient at least two doses per twenty four hours, a first dose for daytime use having a lower concentration of 2-Amino-4,5,6,7-tetrahydrobenzo[b]thiophen-3-yl)(4-chlorophenyl) methanone or a pharmaceutically acceptable salt thereof, and a second dose for nighttime use having a higher concentration of 2-Amino-4,5,6,7-tetrahydrobenzo[b]thiophen-3-yl)(4-chlorophenyl) methanone or a pharmaceutically acceptable salt thereof.

9. The method of claim 7 wherein the first dose for daytime use comprises from 100 to 500 milligrams of 2-Amino-4,5,6,7-tetrahydrobenzo[b]thiophen-3-yl)(4-chlorophenyl) methanone or a pharmaceutically acceptable salt thereof, and the second dose for nighttime use comprises from 500 to 1000 milligrams of 2-Amino-4,5,6,7-tetrahydrobenzo[b]thiophen-3-yl)(4-chlorophenyl) methanone or a pharmaceutically acceptable salt thereof.

* * * * *

UNITED STATES PATENT AND TRADEMARK OFFICE
CERTIFICATE OF CORRECTION

PATENT NO. : 6,248,774 B1  Page 1 of 1
DATED : June 19, 2001
INVENTOR(S) : Edward Leung It is certified that error appears in the above-identified patent and that said Letters Patent is hereby corrected as shown below:

Column 2,
Line 26, before "2-amino", insert -- ( --

Column 3,
Line 19, before "2-amino", insert -- ( --

Column 5,
Line 60, before "2-amino", insert -- ( --

Column 11,
Line 39, before "2-amino", insert -- ( --

Column 12,
Lines 11, 22, 29, 32, 37, and 40, before "2-amino", insert -- ( --

Signed and Sealed this

Twenty-second Day of January, 2002

Attest:

Attesting Officer

JAMES E. ROGAN
Director of the United States Patent and Trademark Office